US00PP14937P2

(12) United States Plant Patent
Schräder

(10) Patent No.: US PP14,937 P2
(45) Date of Patent: Jun. 22, 2004

(54) PETUNIA PLANT NAMED 'SUMPET 03'

(50) Latin Name: *Petunia×atkinsiana*
Varietal Denomination: Sumpet 03

(75) Inventor: Ralf Schräder, Lüdinghausen (DE)

(73) Assignee: Grunewald Veredling B.V. (NL)

( * ) Notice: Subject to any disclaimer, the term of this patent is extended or adjusted under 35 U.S.C. 154(b) by 0 days.

(21) Appl. No.: 10/378,477

(22) Filed: Mar. 3, 2003

(51) Int. Cl.[7] ..... A01H 5/00
(52) U.S. Cl. ..... Plt./356
(58) Field of Search ..... Plt./356

(56) References Cited

PUBLICATIONS

UPOV ROM GTITM Computer Database, GTI JOUVE retrieval software 2003/05 citation for 'Sumpet 03'.*

* cited by examiner

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new and distinct early flowering Petunia plant with good lasting quality and light reddish-purple colored flowers.

2 Drawing Sheets

Botanical classification: *Petunia×atkinsiana.*
Varietal denomination: 'Sumpet 03'.

BACKGROUND OF THE INVENTION

The present invention comprises a new and distinct cultivar of Petunia plant known by the varietal name 'Sumpet 03'. The new variety was discovered in April 2001 in a selected breeding program in Lüdinghausen, Germany designed to produce a new variety of Petunia with a harmonious habit and a new flower color. The new variety was selected from a cross of proprietary unpatented breeding plants Seedling 109 (female parent) and Seedling 97 (male parent). The new variety is a hanging plant as is similar to its parents but differs in flower color than both parents. The new variety was first asexually reproduced in June 2001 by cuttings in Lüdinghausen, Germany. The new variety has been trial and field tested at Lüdinghausen and has been found to retain its distinctive characteristics and remain true to type through successive propagations.

The following trait distinguishes 'Sumpet 03' as a new and distinct cultivar:

1. Flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
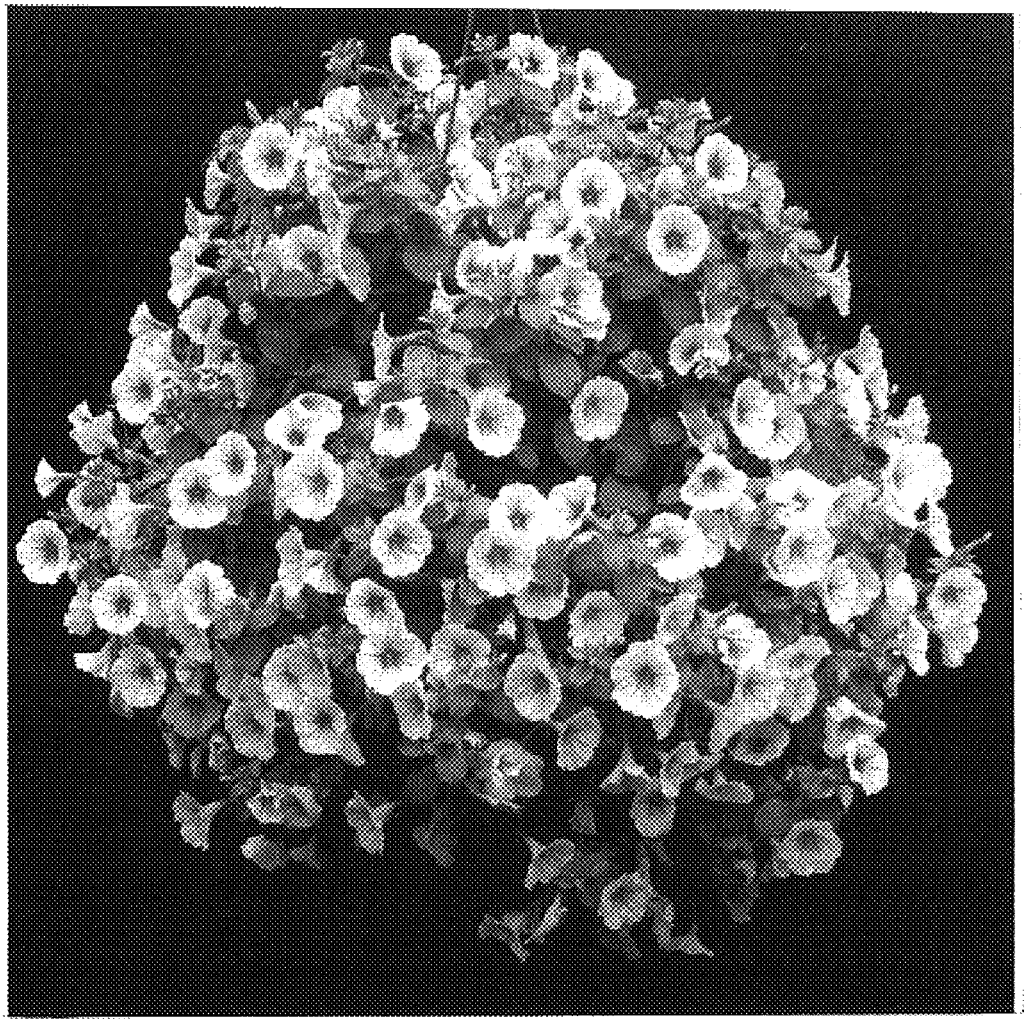
FIG. 1 is a photograph of the plant.
Figure 2:
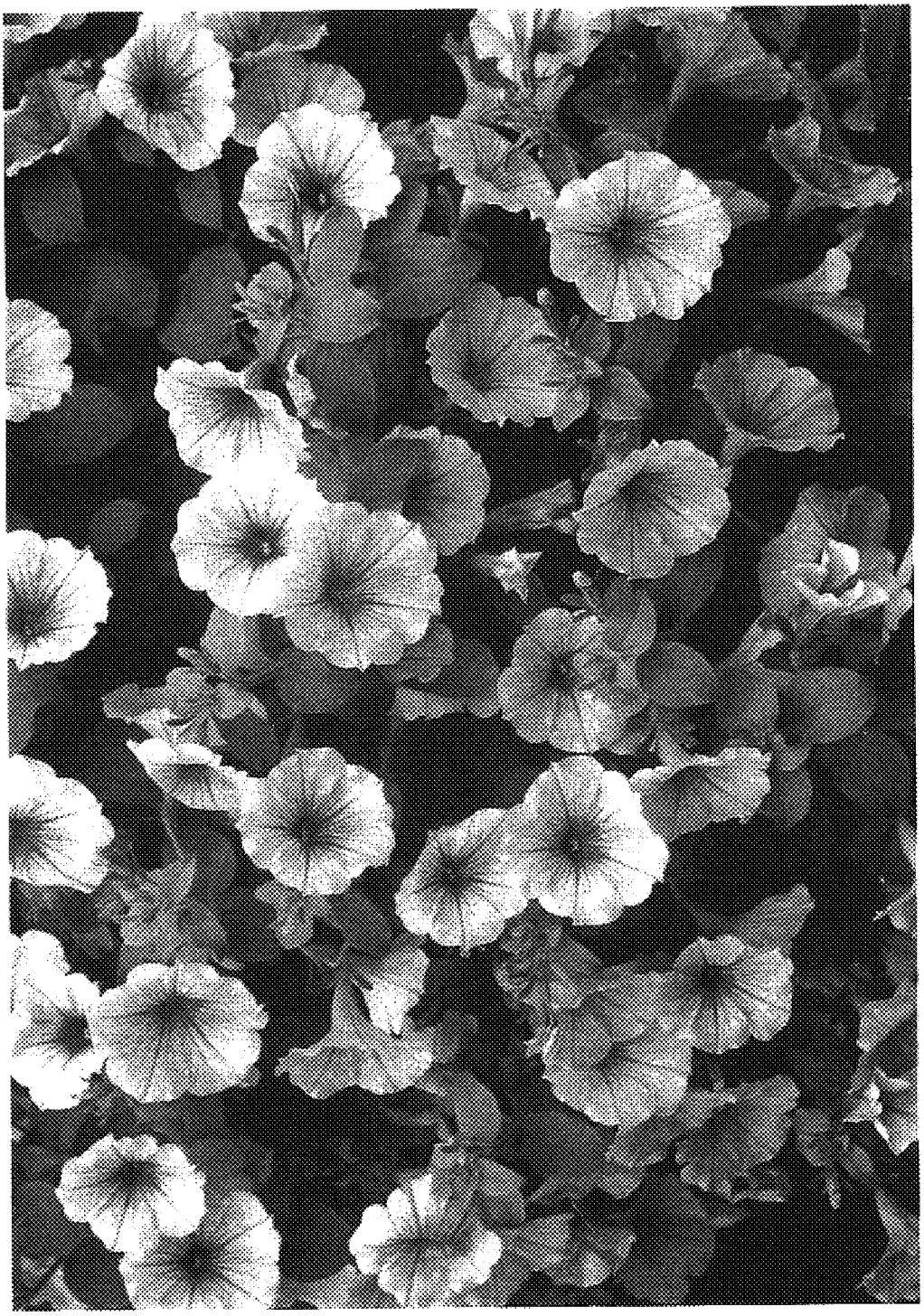
FIG. 2 is a close up view of the blooms of the new plant.

The following detailed description sets forth characteristics of the new cultivar. The data which defines these characteristics were collected by asexual reproductions by cuttings carried out in Lüdinghausen, Germany. Flowering plant were grown in 11 cm containers. Plants for the description were 9 weeks old, grown in a greenhouse at 16° C. temperature. The color readings were taken in a greenhouse under natural light. Color references are primarily to The 2001 R.H.S. Colour Chart of The Royal Horticultural Society of London.

PLANT

Form: Spreading.
Height: 185 mm.
Diameter: 290 mm.
Vigor: Moderate.
Roots:
- *Habit.*—Mounded.
- *Time to initiate roots.*—8 days at 18° C.
- *Time to develop roots.*—15 days at 18° C.

Branching habit: Half-hanging.
Lateral branches:
- *Form.*—Hanging.
- *Color.*—141B.
- *Texture.*—Smooth.
- *Diameter.*—3 mm.
- *Internode length.*—22 mm.
- *Quantity.*—7–8.

Foliage:
- *Arrangement.*—Alternate.
- *Number of leaves per branch.*—23.
- *Shape of leaf.*—lanceolate.
- *Shape of apex.*—Acute.
- *Shape of base.*—Acute.
- *Texture.*—Smooth.
- *Margin.*—Entire.
- *Color.*—Young leaves: Upper surface: 135B. Lower surface: N134B. Mature leaves: Upper surface: 135B. Lower surface: N134B.
- *Petiole.*—Length: 4 mm. Diameter: 2.5 mm. Color: 146B.
- *Veins.*—Color: Upper surface: 146B. Lower surface: 146C.

FLOWER

Natural flowering season: Spring to Autumn.
Number of flowers per plant: 15–17.

Corona:
*Diameter.*—6 mm.
*Flower tube length.*—23 mm.
*Flower tube diameter at distal end.*—12 mm.
*Flower tube diameter at proximal end.*—3 mm.
*Petal length from throat.*—23 mm.
*Petal width.*—24 mm.
*Petal quantity.*—5 parts fused at base.
*Petal apex shape.*—Round.
*Texture.*—Smooth.
*Color.*—When opening: Upper surface: 69C. Lower surface: 69D. Fully opened: Upper surface: 69C. Lower surface: 69D.
*Flower throat* (*inside*).—63B.
*Flower throat, vein.*—63A.
*Flower tube* (*outside*).—152C.
*Flower tube, vein.*—Between 63A and 63B.
*Petal color, fading to.*—62B.

Peduncle:
*Length.*—20 mm.
*Diameter.*—2 mm.
*Color.*—146B.
*Orientation.*—Angled.
*Strength.*—Middle.

Bud:
*Shape.*—Lanceolate.
*Length.*—19–22 mm.
*Diameter.*—5 mm.
*Color.*—140A.

Calyx:
*Shape.*—Cuneate.
*Length.*—15 mm.
*Diameter.*—4 mm.
*Sepal shape.*—Lanceolate.
*Sepal margin.*—Entire.
*Sepal texture.*—Smooth.
*Sepal color.*—Upper surface: 137A. Lower surface: 138A.

Disease resistance: No resistance to diseases noted to date.
Fragrance: None.
Weather tolerance: Good.
Lasting quality: Good.
Seed production: Good.

REPRODUCTIVE ORGANS

Stamens:
*Number.*—5.
*Filament length.*—18–21 mm.
*Anthers.*—Shape: Ovate. Length: 1.1 mm. Color: 142B.
*Pollen.*—Color: 18B. Amount: Heavy.

Pistil:
*Length.*—2 mm.
*Style.*—Length: 23 mm. Color: 146B.
*Stigma.*—Shape: Round. Color: 146A. Ovary color: 146C.

I claim:

1. A new and distinct variety of Petunia plant substantially as shown and described.

* * * * *

UNITED STATES PATENT AND TRADEMARK OFFICE

CERTIFICATE OF CORRECTION

PATENT NO. : PP. 14,937 P2
DATED : June 22, 2004
INVENTOR(S) : Schrader

It is certified that error appears in the above-identified patent and that said Letters Patent is hereby corrected as shown below:

Column 3,
Line 1, "corona" should read -- corolla --

Signed and Sealed this

Twenty-first Day of December, 2004

JON W. DUDAS
*Director of the United States Patent and Trademark Office*